United States Patent [19]

LaConti et al.

[11] 4,123,700
[45] Oct. 31, 1978

[54] POTENTIOSTATED, SELF-HUMIDIFYING, SOLID POLYMER ELECTROLYTE CARBON MONOXIDE DOSIMETER

[75] Inventors: Anthony B. LaConti, Lynnfield; Robert A. Torkildsen, Danvers; Robert C. Jones, Wakefield, all of Mass.

[73] Assignee: General Electric Company, Wilmington, Mass.

[21] Appl. No.: 851,129

[22] Filed: Nov. 14, 1977

[51] Int. Cl.² .................................................. G01N 27/42
[52] U.S. Cl. ...................................... 324/29; 324/182; 204/195 S
[58] Field of Search ............. 324/29, 182; 204/195 R, 204/195 S

[56] References Cited

U.S. PATENT DOCUMENTS

| | | | |
|---|---|---|---|
| 3,613,002 | 10/1971 | Trenkler | 324/182 |
| 3,915,830 | 10/1975 | Isenberg | 204/195 S |
| 4,049,503 | 9/1977 | Becker et al. | 204/195 S |

Primary Examiner—M. Tokar

[57] ABSTRACT

A dosimeter for measuring accumulated dosage of noxious gases, such as carbon monoxide (CO), oxides of nitrogen, ($NO_x$), etc., incorporates a gas-sensing electrochemical cell which utilizes an electrically biased, hydrated, solid polymer electrolyte (SPE) sensing cell. CO and other noxious gases are oxidized at the sensing electrode and the cell current is a measure of the gas concentration. The cell output current is applied to an electrically resettable current integrating device, which is basically an integrating coulometer in which metal is plated onto a working electrode in response to the cell output current. A fixed, reverse calibration current is driven through the coulometer during dosage readout to deplate the metal from the coulometer working electrode. An accurate timing device measures the time required to deplate the working electrode of the coulometer. This product of the fixed calibrating current and the time required to reset the coulometer, i.e., deplate the working electrode is a measure of the gas dosage.

15 Claims, 5 Drawing Figures

POTENTIOSTATED, SELF-HUMIDIFYING, SOLID POLYMER ELECTROLYTE CARBON MONOXIDE DOSIMETER

The instant application relates to a gas-sensing device and, more particularly, to a device for measuring the integrated dosage to which the sensor, and hence the user, has been exposed.

There is a continuing need for instruments which sense gases, such as carbon monoxide, $NO_x$, which are dangerous to health, or gases or vapors, such as alcohol, which are either noxious or represent a social or public health risk. The detection of such gases is becoming ever more important in the industrial sector because of higher and more rigorous health standards in our industrial environment.

Electrochemical gas-sensing devices in which an air sample is brought into contact with catalytic electrodes so that the constituent to be detected is either oxidized or reduced at the electrode with an accompanying exchange of electrons constitute one form of such instruments. Virtually all known electrochemical gas-sensing device utilize corrosive liquid electrolytes and are thus subject to electrolyte leakage. The liquid electrolyte also often masks the electrodes and catalyst sites at which the electrochemical conversion of the gas takes place. Liquid electrolyte cells are also subject to changes in electrolyte concentration during operation. Both of these effects, which are characteristic of gas-sensing cells which utilize liquid electrolyte, seriously affect the performance of the sensor in terms of its sensitivity and response. Furthermore, since the cell electrodes in a sensor which uses a liquid electrolyte must function to contain the liquid electrolyte in the cell, the electrodes must be quite thick and sturdy, thus accounting in part for the cost, bulk and size of the prior art devices.

Two recently filed United States applications for Letters Patent, Ser. No. 773,012 and Ser. No. 773,136, entitled, respectively, "Potentiostatic, Three-Electrode Solid Polymer Electrolyte (SPE) Gas Sensor Having Highly Invariant Background Current Characteristics With Temperature During Zero Air Operation" and "Self-Humidifying, Potentiostatic, Three-Electrode Hydrated Solid Electrolyte Gas Sensor", each filed Feb. 20, 1977 in the names of A. B. LaConti, et al, and assigned to the General Electric Company, the assignee of the present invention, describe a compact, lightweight, electrochemical gas sensors for CO, $NO_x$, alcohol, etc., which are characterized by the use of a potentiostated cell utilizing a hydrated, polymer electrolyte (SPE) membrane. The SPE cell is used in an electrically biased mode, along with a potentiostatic system to maintain the cell sensing electrode at the correct potential to obtain rapid oxidation of the gas to be sensed while at the same time avoiding interference from air due to reduction of oxygen or interference due to the dissociation of water. In the novel gas detectors of the above-referenced LaConti, et al, the counter electrode side of the SPE membrane is flooded with distilled water, so that incoming gases are brought essentially to one hundred percent relative humidity by rapid vapor phase water transport across the membrane, thereby eliminating the need for bubblers or other forms of external humidification. This permits substantial reduction in the size, bulk, and weight of the gas-sensing device. The SPE membrane of the novel LaConti, et al, gas detector includes an ionically conductive, hydrated, SPE bridge formed on one side of the membrane spatially oriented with respect to the reference and sensing electrodes to provide a low-resistance path between these electrodes. As a result, the cell exhibits high output, excellent stability and high sensitivity to the gases to be detected. The sensing and reference electrodes of the LaConti, et al, cells are positioned in such a manner that the reference electrode is positioned outside of the flux field of the sensing electrode. As a result, the temperature characteristics of the cell are substantially more stable than those of existing devices in that no temperature compensation at zero-air conditions (i.e., in the absence of the gas to be detected) is required. This results in substantial simplification of the temperature compensating circuitry for the gas-sensing device in that accurate indications over the entire operation or span range is possible with the use of but a single thermistor for span signal temperature compensation. The electronic circuitry associated with the electrochemical gas-sensing detector is therefore simplified, also leading to reductions in the size and the cost of the device.

Applicant has found that the SPE gas-detecting electrochemical cell described and claimed in the above-identified LaConti, et al, application is ideally suited for use in a gas monitoring assembly which is capable not only of sensing gas concentration, but which also provides indication of total exposure, i.e., the integrated value (dosage) of the sensed gas. It has been found that this may be readily achieved by utilizing gas-sensing cell in combination with an electrically resettable integrating device of the coulometer type. Applicant has also found that when combined with a SPE cell, all of these desirable characteristics may be provided in a dosimeter arrangement which is very small and compact. So compact, by virtue of the unique SPE cell configuration and circuitry, that size and weight reductions are sufficient to reduce the size of the dosimeter to one which may be carried in the skirt pocket of the user.

It is, therefore, a principal objective of the instant invention to provide a gas-detecting apparatus using solid polymer electrolyte gas-sensing cells which are capable of providing total exposure or dosage information.

Another objective of the invention is to provide a gas dosimeter utilizing a solid polymer electrolyte gas-sensing cell and a dischargeable integrating device for recording dosage.

Still another objective of the invention is to provide a dosimeter utilizing a solid polymer electrolyte gas-sensing cell which also provides the visual and audible indications whenever the concentration of the gas exceeds predetermined levels.

Yet a further objective of the invention is to provide a gas dosimeter utilizing a solid polymer electrolyte gas-sensing cell which is small, compact enough to be worn by the user and has low power consumption during standby operation.

Yet further objectives and advantages of the instant invention will become apparent as the description thereof proceeds.

The various objectives and advantages of the invention are realized in a gas-detecting arrangement which uses a potentiostated, solid polymer electrolyte gas-sensing cell. The output signal from the sensing cell is applied to an integrating coulometer. A metal, such as silver, is plated onto one of the electrodes of the coulometer in response to the output signal from the cell, thus storing the information. This plating action continues as long as there is an output from the sensing cell, thereby providing an integrating action. Dosage information is read out from the coulometer by driving a fixed, reverse calibration current through the cell to deplate the electrode. With the fixed reverse current being driven through the coulometer, the total exposure is determined from the product of the constant current, $i$, and the time, $t$, required to completely deplate the integrating coulometer and reset it to its zero integral level.

A support console is associated with the dosimeter and includes a source of fixed calibration current as well as synchronized timing and counting circuitry to determine the time interval during which the reverse calibration flows to deplate the coulometer. This information relating current magnitude and time is then a dosage indication.

The novel features which are believed to be characteristic of this invention are set forth in the appended claims.

The invention itself, however, both as to organization and mode of operation, together with further objectives and advantages thereof, may best be understood by reference to the following descriptions taken in connection with the accompanying drawings in which.

Figure 1:
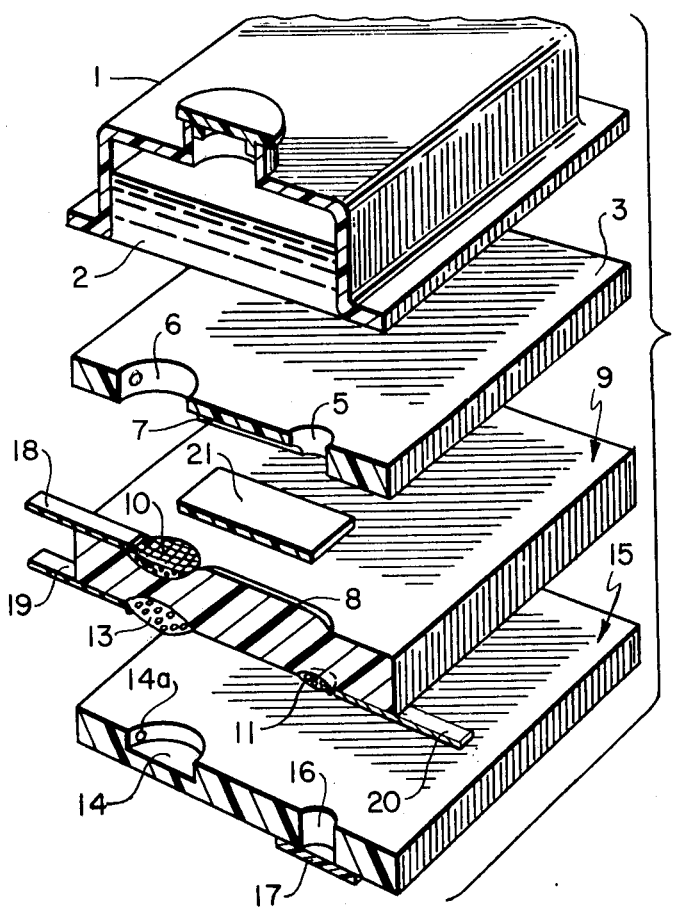
FIG. 1 is an exploded view of the solid polymer electrolyte gas-sensing cell.

The thermally stable, self-humidifying, electrically biased, potentiostated, three-electrode, SPE gas-sensing cells used in the instant invention and described and claimed in the two aforesaid LaConti, et al, applications are based upon the oxidation or reduction of the gaseous constituent to be detected at a catalytic sensing electrode. The sensing electrode, in the operational mode, is maintained at a potential to produce rapid oxidation or reduction of the gaseous constituent to be detected. In the case of carbon monoxide detection, carbon monoxide is rapidly oxidized at the sensing electrode to form carbon dioxide with the release of electrons so that the cell current is a measure of the CO concentration. The reference electrode is biased to maintain the potential more anodic than the rest potential of an electrode for air, so that reduction of oxygen in the air has no, or at least a minimal, effect on the cell output. The sensing electrode potential, however, must be more cathodic than the potential at which water is dissociated to produce hydrogen and oxygen to avoid interference from this source. In the case of carbon monoxide, the potential for the $CO/CO_2$ redox couple is $-0.12$ volts with reference to a $Pt/H^+$ reference electrode. By maintaining the potential of the sensing electrode, in the range between 1.0 to 1.3 volts, there is rapid and almost instantaneous oxidation of carbon monoxide reaching the sensing electrode according to the following rections:

SENSING ELECTRODE $$CO + H_2O = 2H^+ + CO_2 + 2e^- \quad (1)$$

COUNTER ELECTRODE $$2H^+ + 2e^- = H_2, \text{ or} \quad (2)$$
$$2H^+ + \tfrac{1}{2}O + 2e^- = H_2O \quad (3)$$

It can be seen from the above reaction that electrons are released as carbon monoxide is oxidized to carbon dioxide. This current flow in the external circuit due to the rapid oxidation of carbon monoxide is directly related to the concentration, in parts per million, of carbon monoxide. With the potential at the sensing electrode limited to 1.3, the sensing electrode is not sufficiently anodic to oxidize water and introduce errors due to current produced by the oxidation by this couple. The theoretical oxygen/water redox couple is 1.23 volts. Howver, the oxidation of water takes place at some voltage greater than the theoretical 1.23 volts. For the platinum-five percent iridium catalyst used in the instant sensor, there is minimal or no oxidation of water at 1.3 volts, thereby ensuring that the current flow is due exclusively to the oxidation of carbon monoxide. Since this voltage also exceeds the rest potential of oxygen, no reduction of oxygen takes place in the entire range and no interference due to air is encountered.

It will also be appreciated that the sensor and the dosimeter, presently to be described, are also capable of selectively detecting other gases or vapors such as alcohol, NO, $NO_2$, $H_2$, depending on the catalyst, the biasing voltages at the sensing electrodes, etc. The biasing voltages for different gases are similarly related to the redox couple for the particular gaseous constituent to be sensed and the range of overvoltages for the particular catalytic electrode. The reference, sensing, and counter electrodes of the cell are maintained at the desired potentials by means of potentiostatic circuitry presently to be described.

FIG. 1 shows an exploded, perspective view of the gas-sensing cell utilized in the dosimeter of the instant invention. The sensing cell is of the self-humidifying type described in the two aforesaid LaConti, et al, applications. The cell includes a reservoir 1 which is filled with distilled water and is in firm contact with upper surface of a gasket 3. Gasket 3 contains a pair of hydration ports 5 and 6 connected, on the underside of gasket 3, by means of a water channel 7. Channel 7 is located over an ionically conductive, hydrated, bridge 8 formed integrally along the upper surface of a hydrated, SPE cation exchange membrane 9. Hydration port 5 is aligned spatially with one end of bridge 8 and hydration port 6 is spatially aligned with a counterelectrode 10 at the other end of the bridge. Counterelectrode 10 is a catalytic electrode which is bonded to and embedded in the upper surface of membrane 9. Thus, bridge 8 extends from counterelectrode 10 to a point directly opposite a catalytic reference electrode 11, bonded to and embedded in the lower surface of membrane 9. Hydration port 6 is somewhat larger in area than counterelectrode 10 so that the surface of the counterelectrode and the membrane around it is flooded by distilled water from the reservoir. Consequently, water in vapor phase diffuses rapidly through the membrane to the other side in the vicinity of a sensing electrode 13 which is also bonded and embedded in the lower surface of membrane 9 and is in spatial alignment with counterelectrode 10. A gas stream containing the constituent to be detected is brought into a circular chamber 14 in the surface of a bottom plate 15 through opening 14a. A sampling pump or other device brings the sample into the chamber through opening 14a. The sample in chamber 14 is thus brought into contact with sensing electrode 13. Reference electrode 11 which is also bonded to the underside of membrane 9 is in direct communication with an opening 16 which is covered by a silicone barrier film 17. Film 17 permits passage of oxygen or air to the reference electrode while blocking the gaseous constituent which is to be sensed as, for example, carbon monoxide. That is, access to the reference electrode is through a film which selectively blocks the gaseous constituent to be detected.

Each of the electrodes has suitable conductive tabs 18, 19, and 20. These tabs are connected to the potentiostatic circuitry associated with the cell, presently to be described, as well as the remaining circuitry of the dosimeter. An adhesive tape 21 is positioned between gasket 3 and membrane 9 at a location away from the electrodes and hydrated bridge 8 in order to fasten the gasket and membrane 9 securely together. A similar adhesive tape, not shown, is positioned between the lower surface of membrane 9 and the bottom plate 15. This tape is located between electrodes 11 and 13 to secure the membrane to the bottom plate and to block flow of gas between the reference and sensing electrodes. This, of course, may be achieved other than by means of an adhesive tape, although an adhesive tape is a simple and ready solution to the problem.

The swollen, hydrated, ionically conductive bridge 8 extends along the lateral surface of the membrane from electrode 10 to a point on the upper surface which is spatially aligned with reference electrode 11 embedded in the lower surface of membrane 9 in order to provide a good, ionically conductive path from sensing electrode 13 which is aligned with the counterelectrode. This path is then from the sensing electrode through the membrane to the counterelectrode along the bridge 8 through the membrane and to reference electrode 11. This provides a low-resistance path between the reference and sensing electrodes substantially eliminating or minimizing IR drop between the sensing and reference electrodes. This will eliminate or minimize changes in the fixed voltage differential maintained between the sensing and reference electrodes. As a result, the instrument sensitivity is high so that it produces a high output even with very low gas concentrations. Furthermore, the instrument is highly invariant with time and is not subject to background current errors at zero-air operation due to temperature changes.

The cell is also constructed, as was pointed out in the aforesaid LaConti, et al, application, so that the sensing and reference electrodes are preferably on the same side of the membrane. They are positioned as closely together as possible, while at the same time making sure that the reference electrode is not affected by the current flux lines between the sensing and counterelectrodes as the potentiostatic circuit drives current from the counter to the sensing electrode to maintain the electrode potential and the voltage differential constant.

The solid polymer electrolyte, ion exchange membrane 9, is preferably a perflourocarbon sulfonic acid membrane which has excellent ion exchange capacity, has high stability, is resistant to acids and strong oxidants, and has excellent thermal stability. One preferred form of such a cation membrane is one in which the polymer is a hydrated CO-polymer of polytetraflourethylene (PTFE) and polysulfonyl flouride vinyl ether containing pendent sulfonic acid groups. One form of such a solid polymer electrolyte is sold commercially by the DuPont Company under its trade designation "Nafion".

Electrodes 10, 11, and 13, in the form of a decals of catalytic material mounted on current collecting screens, are integrally bonded to and embedded in the surface of the polymeric cation exchange membrane. The catalytic electrodes are preferably gas permeable, noble metal alloyed particles bonded to particles of a hydrophobic polymer such as polytetraflourorethylene. Catalytic electrodes preferred for CO oxidation are preferably a bonded mixture of reduced oxides of a platinum-5% iridium alloy and PFTE hydrophobic particles. Reference is hereby made to U.S. Pat. No. 3,992,271 Danzig, et al, issued Nov. 16, 1976 and assigned to the General Electric Company, the assignee of the present application, for the detailed description of a fabrication process for the reduced oxides of platinum iridium.

Figure 2:
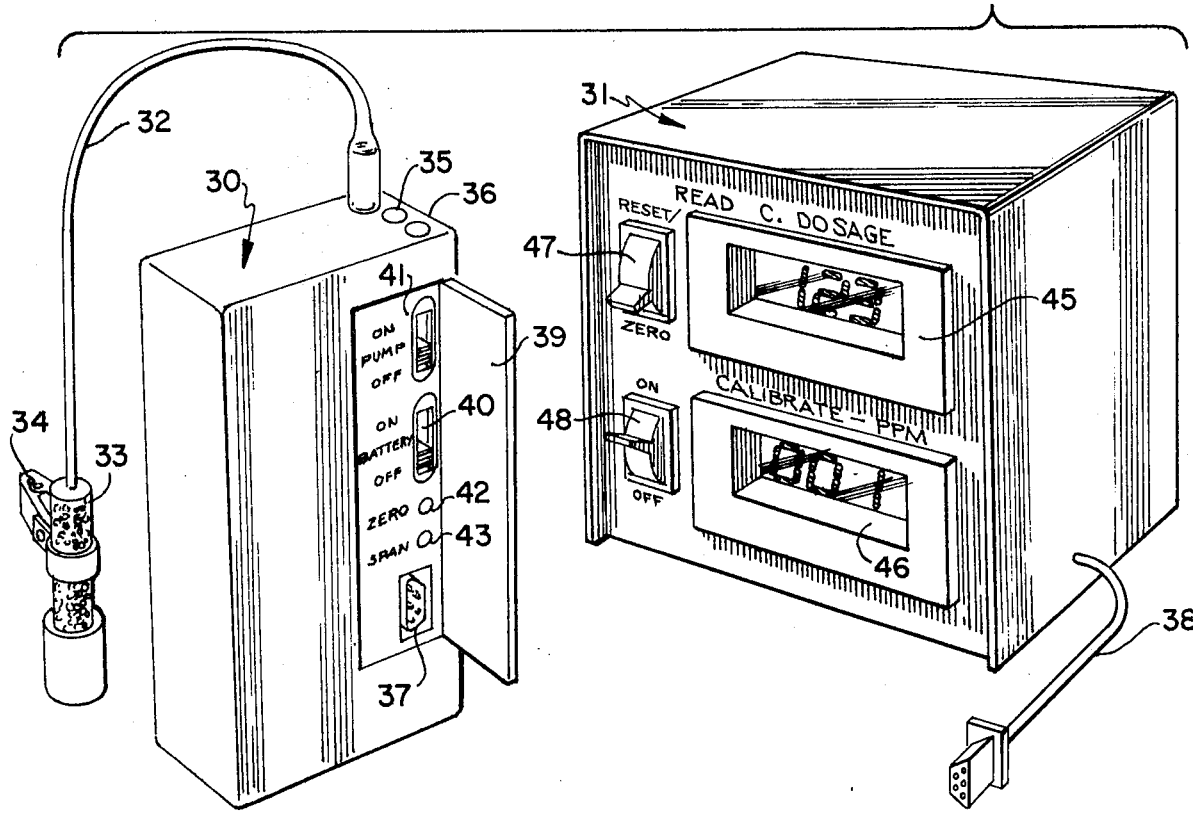
FIG. 2 is a prospective view of the dosimeter and the support console.
Figure 3:
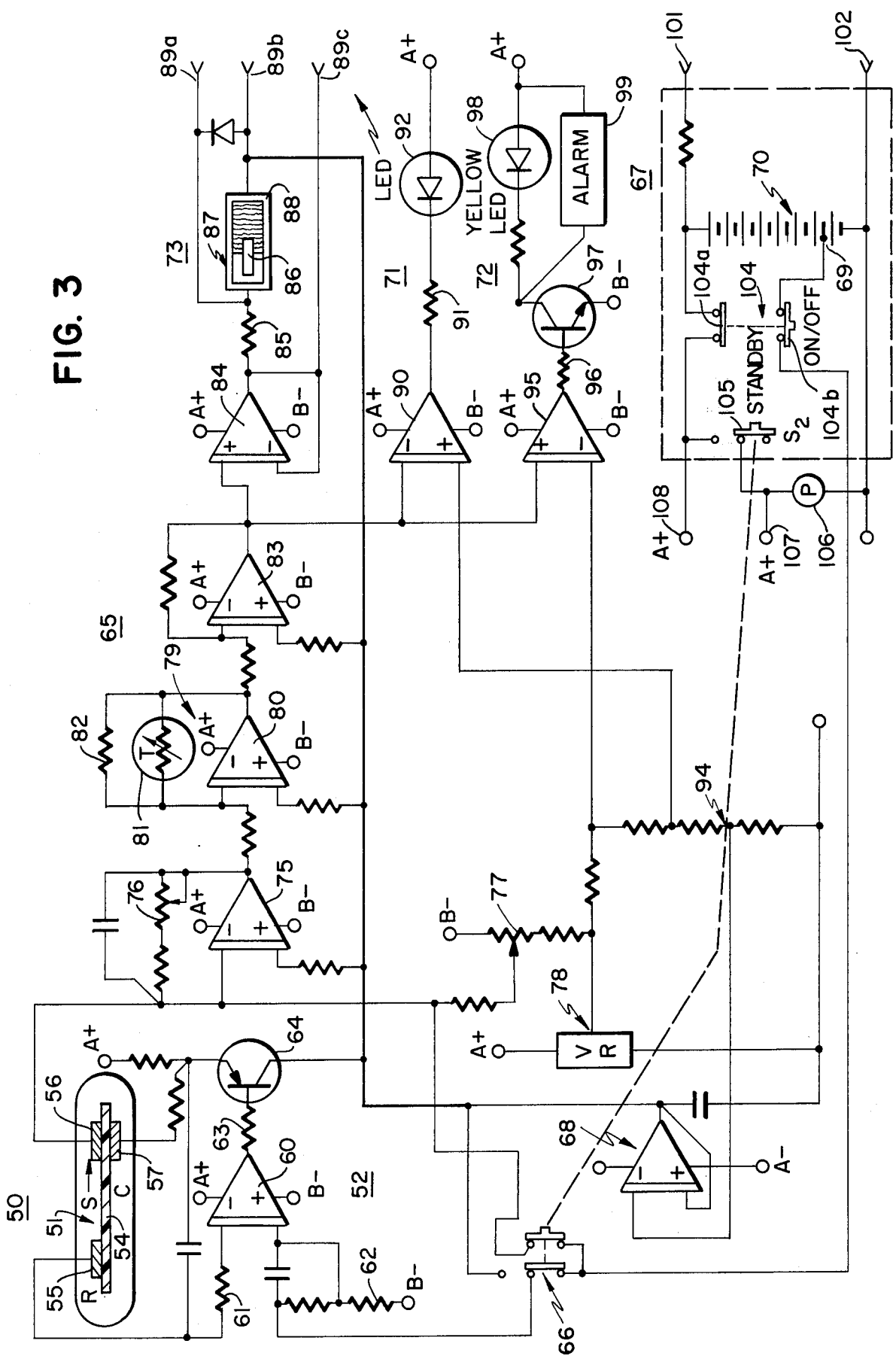
FIG. 3 is a schematic illustration of the dosimeter cell and associated circuitry.

This electrochemical gas-sensing cell forms part of a dosimeter in which total exposure to the gas to be detected may be indicated. The current resulting from the electrochcmical oxidation of carbon monoxide is directly related to the quantity of the CO in the air sample to which the sensing electrode of the cell of FIG. 1 is exposed. The signal from the sensing electrode is stored in an electrically dischargeable integrating dosage element such as an integrating coulometer. The signal from the sensing cell is also utilized to produce a visual or audible indication whenever the concentration of the gas reaches one or more predetermined levels which warrant a caution or warning indication to the user that the particular concentration level has been reached. The dosimeter to be described presently in connection with FIGS. 2 and 3 is associated with a support console in which the total dosage may be read out and indicated. To this end, the console provides a source of constant current which is used to reset the integrating coulometer when dosage readout is desired. It also includes a timing device which determined the duration of the flow of the constant current necessary to reset the integrating coulometer. Total exposure to the gas (or dosage) is then determined from the product of the fixed calibration current driven through the coulometer and the time required to reset the integrating coulometer to its zero integral level.

FIG. 2 shows a perspective view of the dosimeter device 30 and support console 31. Dosimeter 30 contains the electrochemical gas-sensing cell, a sampling pump, electronic circuitry for producing a signal proportional to the cell output, and an electrically resettable integrating coulometer which measures total exposure during the operating period, as well as visual and audible alarms which are actuated when the concentration of the gas exceeds predetermined levels.

Dosimeter 30 includes a sampling tube 32 connected to the dosimeter housing. A sampling pump in the housing pulls a gas-sensing sample through tubing 32 and a scrubber cartridge 33 attached to the end of the tube. The scrubber material in cartridge 33 is selective to the particular gas to be sensed. Thus, for a carbon monoxide detector, the scrubber 31 may be filled with particles of potassium permanganate on alumina, an oxidant which scrubs all gases but hydrogen and carbon monoxide. Even though some hydrogen will pass through the scrubber, the sensitivity of a hydrated SPE cell to hydrogen is 100 times less than it is to carbon monoxide. Any hydrogen which passes through the scrubber thus has very little effect on the accuracy of the device.

Thus, for all practical purposes, potassium permanganate on alumina is CO selective. This material is commercially available under the trade name "Purefill" sold by Purefill, Inc., a subsidiary of H. E. Burroughs Company.

Scrubber cartridge 33 has a mounting clip 34 which may be attached to the collar or other portion of the wearing apparel of the user. Positioned at the top of dosimeter housing 30 are visual indicators 35 and 36 which take the form of amber and red light emitting diodes. These visual indicators are energized to produce either an amber or red light whenever the concentration of the carbon monoxide exceeds a predetermined level. Amber light emitting diode 35 is energized whenever the first, lower predetermined level is reached and the red light emitting diode 36 is energized when a second higher concentration level is exceeded. Whenever the red light emitting diode is energized, the system also produces an audio alarm so that a buzzing sound to indicate that the CO concentration has reached a different predetermined and higher level.

The dosimeter controls, and a cable connector 37, for connecting the dosimeter to the support console through a cable 38, are located behind a door 39 in the dosimeter housing. Mounted in a receptacle covered by door 39 is a battery slide switch 40 which controls power to the dosimeter. With switch 40 in the ON position, the dosimeter is fully "operational" or on "standby", depending on the position of "pump" switch 41. With switch 40 in the OFF position, the dosimeter is completely disabled. With switch 40 in the ON position, and switch 41 in the OFF position, the dosimeter is in a "standby" mode and the sampling pump is de-energized. During this "standby" mode, the sensing cell remains energized, but all the other circuits are de-energized. As a result, the current drain during "standby" is very low while allowing rapid dosimeter warm-up when the device is switched into the fully operational mode by switch 41. When switch 41 is in the ON position, the pump and all other circuits are energized and the dosimeter is fully operational. Potentiometer adjusting screws 42 and 43 are provided to allow adjustment calibration of the instrument at zero air-flow conditions and over the range or span of the instrument.

Support console 31 shows the accumulated gas dosage on a digital display 45. Console 32 also has a display 46 which shows gas concentration in PPM for dosimeter calibration. Console switch 47 controls dosage readout. When switch 47 is in the reset/read position, a fixed calibrating current from the console is supplied to the dosimeter to allow the coulometer to be reset and the dosage to be displayed. When switch 47 is in zero position, the display is cleared. Console switch 48 controls power to the support console and controls battery charging current to the dosimeter. With switch 48 in the ON position, power is supplied to the console and battery charging current is supplied to the dosimeter battery through cable 38. With switch 48 in the OFF position, all power is cut off and the entire console is disabled.

The dosimeter of the instant invention is illustrated schematically in FIG. 3 and includes a gas-detecting cell assembly 50 which incorporates a gas-sensing electrochemical cell 51 controlled by potentiostatic circuit 52. Cell 51 is a three-electrode, hydrated, solid polymer electrolyte (SPE) cell which is used as the sensor to detect selected gases such as CO, etc. Electrochemical cell 51 is operated in a potentiostated, electrically biased mode to produce a stable output proportional to concentration of the gas in the air sample. Cell 51, which is of the type described and claimed in the aforesaid LaConti, et al, application, has a cation exchange membrane 54 with a catalytic reference electrode 55 and a catalytic sensing electrode 56 bonded to and embedded in one surface of the membrane. A catalytic counterelectrode 57 is positioned on the opposite surface of the membrane and in spatial alignment with sensing electrode 56. The three-electrode cell assembly 51 has a potentiostatic circuit 52 associated therewith to maintain the potentials at the sensing and reference electrode at predetermined values to provide an output which is directly related to the gas concentration.

Potentiostatic circuit 52 maintains the potential at the sensing electrode at the proper level to produce rapid oxidation of the gas to be sensed. This results in a current from the counter to the sensing electrode which is directly related to the gas concentration. At the same time, the potential at the sensing electrode is sufficiently cathodic to prevent any current flow due to the dissociation of water by electrolysis. Similarly, the sensing electrode potential must be sufficiently anodic (approximately 1 to 1.1 volts) vs. $Pt/H^+$ electrode to avoid interference from air due to the reduction of oxygen at the sensing electrode. The potentiostatic circuit also maintains a potential difference between the sensing and reference electrode which is sufficient to provide adequate sensitivity.

Potentiostatic circuit 52 includes an operational amplifier 60. The inverting terminal of amplifier 60 is connected through a current limiting resistor 61 to cell reference electrode 55. The non-inverting terminal of amplifier 60 is connected to a reference voltage divider 62 which provides a reference voltage to which the potential at the reference electrode is continuously compared to produce an output signal which is supplied through a current limiting resistor 63 to the base of a PNP transistor power amplifier 64. The emitter of trantsistor 64 is connected to counterelectrode 57 and drives current between the sensing and counterelectrode in order to maintain the sensing electrode at the desired potential.

The output of cell 51 is applied as an input signal to a signal processing network 65 where the signals are scaled, amplified, and compensated for shifts in sensor-span signal due to temperature.

One terminal of reference voltage divider 62 is connected through a pair of ganged slide switches 66, either to multistage power supply 67, or to regulated voltage source 68. The other terminal of voltage divider 62 is connected to the B-supply bus of power supply 67. During "standby", slide switch 66 (as shown in FIG. 3) connects the upper terminal of voltage divider 62 to tap 69 of a battery 70 which forms part of power supply 67. This maintains the cell energized, but the voltage differential between the reference and sensing electrodes is less than that maintained during the operating mode. In the "operating" mode, switch 66 is moved up and connects voltage divider 62 to regulated voltage source 68, so that the reference voltage applied to amplifiers 60 in the potentiostatic circuit drives the circuit to maintain the desired voltage differential between the electrodes.

This arrangement also provides a built-in test (bit) feature which shows whether the concentration level alarm circuits, presently to be described, are functioning properly. This bit feature is used whenever the dosimeter is switched from the "standby" to the "operating" mode as would be the case when a dosimeter is given to a user at the beginning of a work shift, for example.

During "standby" with voltage divider 62 connected to tap 69 of power supply battery 70, the cell is only partially energized in that the sensing electrode is maintained at the potential difference with respect to the reference electrode which is less than that required for normal operation. For example, in the "operate" mode, the electrode potential difference is, for example, 56 MV. During "standby", the reference and sensing electrode potential differential from tap 69 is only 40 MV. When the dosimeter is switched from "standby" to "operate", the voltage applied to voltage divider 62 from regulated voltage source 68 is greater than that from tap 69. The potentiostat drives current between counterelectrode 57 and sensing electrode 56 to bring the potential at the sensing electrode to the desired level and to bring the potential difference between the sensing reference electrode to the desired 56 MV. This current, which changes the voltage at the sensing electrode, simulates oxidation of CO and is applied to the input to signal processing network 65. This signal simulates a concentration of carbon monoxide which is in excess of the levels at which warning indications are to be produced. As a result, all of the alarms in concentration level indicating networks 71 and 72 are actuated if they are functioning properly. As the dosimeter warms up and the potential at the sensing electrode and the voltage differential between the sensing and reference electrode reach the proper values, the signal at the sensing electrode is reduced to zero since, under normal conditions, there would not be any carbon monoxide. The simulated signal is thus removed from network 65 and from networks 71 and 72 causing the alarms, both visual and audible, to terminate. Thus, an operational check is provided whenever the dosimeter is switched from "standby" to "operate" to ensure that the alarm or indicating circuits are functioning properly.

Of course, whenever the air sample passed over the sensing electrode by the scrubber and pump arrangement contains the gas to be sensed (i.e., CO, etc.), the oxidation of the gas at the sensing electrode produces an output which is directly related to the gas concentration and this signal is applied to signal processing network 65. The output from network 65 is applied to a gas dosage recording 73 in which the instantaneous carbon monoxide concentration signals are integrated to provide accumulative total of exposure to carbon monoxide. Gas dosage recording network 73 includes an electrically resettable integrating element in the form of an integrating coulometer in which the signals are stored. The resettable coulometer, presently to be described in detail, provides a history of exposure to the gas which may, in turn, be displaced as a time-weighted average in PPM-hours.

The output signal from network 65 is, as pointed out previously, applied to level indicating networks 71 and 72 to produce an output indication whenever the gas concentration exceeds predetermined levels. Thus network 71 is set to produce a visible warning indication whenever the concentration exceeds a first level, such as 100 PPM of CO, for example. Network 72 is set to produce a warning indication, in this instance both visual and audible, whenever the concentration exceeds a second, higher level, such as 200 PPM, for example. The output signals from network 65 are compared in networks 71 and 72 with reference level signals which are representative of the predetermined concentration level to an alarm signal regenerated to produce the alarms when the signal from network 65 indicates that the concentration sensing by the cell has exceeded the predetermined level or levels.

SIGNAL PROCESSING NETWORK 65

The output current from sensing electrode 56 of cell 51 is applied to the inverting terminal of a scaling amplifier 75. A span adjusting potentiometer 76 and bypass capacitor in parallel therewith is connected in a negative feedback path from the output of the amplifier to the inverting terminal. This feedback network provides overall span adjustment for the instrument. Thus, if the span is from 1 to 500 PPM, for example, the span adjustment potentiometer is adjusted to obtain the required signal level at 89c. Operational amplifier 75 also has its inverting input terminal coupled to a calibrating potentiometer 77 to provide zero adjustment or calibration of the instrument. When the instrument is calibrated for zero-air operation (i.e., with high purity air containing less than one part per million of carbon monoxide), potentiometer 77 is adjusted so that the instrument output indication is also zero. Potentiometer 77 is connected between the power supply B-bus and the output of voltage regulator 78.

The output from amplifier 75 is applied to a sensor signal temperature compensating amplifier network 79. Temperature compensating network 79 is provided to correct for shifts in sensor signal due to changes in temperature. As was pointed out in the above referenced LaConti, et al, applications, the SPE gas-detecting cell described there has excellent temperature characteristics for zero-air operation, so that no temperature compensation is required for this condition. Temperature does, however, have an effect on the sensor signal and errors can be introduced with temperature changes, unless the signal is properly compensated. Network 79 provides this compensation. The network includes an operational amplifier 80 to which the output signal from amplifier 75 is coupled. The temperature compensating network includes a thermistor 81 and a resistor 82 connected in parallel in a negative feedback path from the output of amplifier 80 to its input. The combination of thermistor 81 and resistor 82 controls the gain of amplifier 80. The resistance variation with temperature of the thermistor-resistor combination in the negative feedback path is equal to and opposite in sign to the sensor signal variations which varies the gain of the amplifier correspondingly and cancels the error in the sensor signal due to temperature changes. Hence, the output from amplifier 80 is an accurate representation of the carbon monoxide concentration regardless of the ambient temperature variations. The temperature compensated signal at the output of amplifier 80 is applied to an operational amplifier 83 which is a buffering stage between the signal processing network and the gas concentration level indicating networks 71 and 72 and dosage recording network 73.

GAS DOSAGE RECORDING NETWORK 73

Network 73 includes an operational amplifier 84 which receives the carbon monoxide concentration signal from network 65. The output of amplifier 84 is applied to a large resistor 85 to convert the voltage from amplifier 84 to a current representing the level of the input signal from amplifier 83 to the network. This current is applied to an electrically resettable integrating coulometer 87 which stores the signal and thus records dosage. Coulometer 87 integrates electron flow in either direction retaining the last integral or set charge indefinitely.

Figure 4:
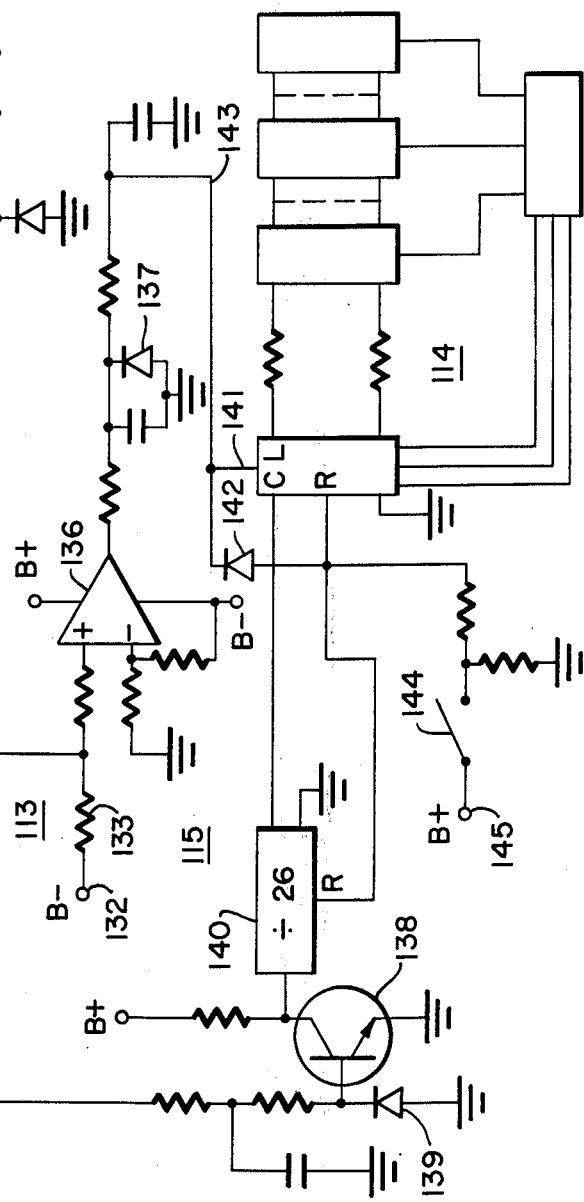
FIG. 4 is a schematic illustration of the electrically dischargeable gas dosage integrating cell and a graph showing the voltage characteristics of the integrating device.

The particular, resettable, integrating coulometer shown schematically at 87 and in FIG. 4 consists of a silver case 88 which serves three separate functions; that of an electrode, that of a reservoir of active metal (silver), and that of a container for the electrolyte. This case is, therefore, normally denominated as the reservoir electrode. The electrolyte inside of the casing serves as a vehicle for ion conduction between the electrodes, this being the only electron transfer process that occurs. Electrode 86, which is usually denominated as the working electrode, is made of gold. One atom of silver from casing 88 or the electrolyte is electroplated onto (integral increase) the gold working electrode whenever electrons enter the gold working electrode and leave through the silver case or reservoir electrode. The electron current from amplifier 84, which represents the CO concentration, enters through the working electrode 86 which is maintained at a reference potential, and leaves through case 88, thus depositing one atom of silver on electrode 86 for every electron which enters. One atom of silver is removed (integral decrease) from the working electrode when the current polarity is reversed; namely, when electrons enter the case and leave through the working electrode.

As will be pointed out later, when CO dosage is read out from the coulometer, a fixed calibrating reverse electron current from the console is driven through coulometer 87 from the outer casing to working electrode to deplate the working electrode. When the coulometer integral is zero, i.e., all of the silver has been removed from the gold working electrode, no further ion conduction can occur and the integrating coulometer becomes an electrical open circuit. It may be seen from the curve of FIG. 4, during the period when silver is being either plated or deplated from the working electrode, the voltage across the cell is low as shown by portion A of the curve. Whenever the zero integral state is reached; namely, when all silver has been removed from the working electrode, the voltage across the cell rises sharply as shown at portion B of the operational curve of FIG. 4. This change in potential provides a triggering signal which indicates that all of the silver has been removed and that the integrating coulometer has been reset and is ready for normal operation.

In operation, the current from amplifier 84 and resistor 85 plates the working electrode as long as the dosimeter is in the "operate" mode and this action continues and the information remains stored. On readout, a fixed, reverse, calibration current from the support console (or other source) is coupled to the case of the coulometer. Total exposure is then determined from the product of the constant reverse calibrating current, $i$, and the time, $t$, required to reset the integrating coulometer to the zero integral level. Console 31 includes a fixed current source which is coupled to the cable connectors 89a and 89b. Whenever the coulometer is reset by applying the reverse calibrated current from the console, a timing mechanism and counter in the console is simultaneously actuated. Each count of the counter represents a fixed time period and also 1 part per million-hour. The counter keeps counting as long as the current flows. When all of the silver is deplated, coulometer 87 is reset. When integrating coulometer 87 reaches this zero integral level, the rise in potential across the coulometer is utilized as a triggering signal to terminate counting. The final count thus represents time $t$, required to discharge the coulometer completely with a calibrated current, $i$. This product of current and time ($t \times i$) is calibrated to indicate directly the dosage, in part per million hours, to which the dosimeter has been exposed.

Electrically dischargeable, integrating coulometers of the type described, are available commercially. One such commercially available device is known by the trade designation "E-Cell" is manufactured and distributed by Plessey Electrode Products, a subsidiary of Plessey, Inc., of 3860 Centinela Avenue, Los Angeles, Calif.

CONCENTRATION LEVEL ALARM NETWORK 71

Network 71 produces a visual indication whenever the CO concentration exceeds a first, predetermined level such as 100 PPM, for example. Network 71 includes an operational amplifier 90 which compares the output signal from network 65 with a reference signal from voltage divider 94 representing the preset CO concentration at which a warning is desired. If the sensor signal at the output of network 65 is larger than the reference signal, indicating that the concentration exceeds the predetermined level of 100 PPM, the output of amplifier 90 goes negative. The output of amplifier 90 is applied through current limiting resistor 91 to the cathode of a light emitting (LED) diode 92, the anodes of which is coupled to a positive supply terminal A+ from the dosimeter power supply, thus causing diode 92 to emit a light indication.

The reference voltage from reference voltage divider 94 is applied to the non-inverting terminal. Voltage divider 94 is connected between the positive output from a voltage regulator 78 and the B-bus of the power supply. If the output signal from network 65 is smaller than the reference potential, then the output of amplifier 90 is positive and light emitting diode is de-energized. When energized, light emitting diode 92 emits light of a given color, such as amber, for example. Thus, when the first predetermined gas concentration is reached, the amber light goes on and remains on until the carbon monoxide concentration drops below that predetermined level. Thus, a warning light is provided to the wearer and user whenever the CO concentration exceeds the first predetermined level.

CONCENTRATION LEVEL ALARM NETWORK 72

In a similar manner, the output signal from network 65 is applied to an operational amplifier 95 in network 72 where it is compared with a further reference signal from voltage divider 94. The cell output signal and reference signals applied, respectively, to the noninverting and inverting terminals of amplifier 95. The output of amplifier 95 is coupled through current limiting resistor 96 to the base of an NPN transistor 97. The collector of transistor 97 is connected through a current limiting resistor to the cathode of light emitting diode 98 which emits red light when energized. The output of amplifier of transistor 97 is also connected to an audible alarm 99 connected in parallel with LED 98. Whenever the output voltage from network 65 is smaller than the reference voltage, the output of the amplifier is negative and NPN transistor 97 does not conduct. Neither light emitting diode 98 nor audible alarm 99 are energized. When the cell output signal is larger than the reference signal, the output of amplifier 95 is positive and transistor 97 conducts heavily. The cathode of LED 98 is made sufficiently negative from A+ bus to energize the diode and cause it to emit red light at the same time alarm 99 is energized. Both a visual and audible alarm thus indicate to the user that a sound, predetermined and higher concentration level has been exceeded.

LED 98 and alarm 99 remain energized to provide the warning indication as long as the concentration exceeds the predetermined level. It will also be obvious that when the second predetermined level is reached to energize network 72, light emitting diode 92 in network 71 will have been energized earlier. Thus, when the CO concentration exceeds the second, higher level, both diodes are energized and provide visual indications. Simultaneously, the audible alarm sounds to provide additional warning to the user that a second, higher concentration level has been exceeded.

SELECTABLE MULTIPLE OUTPUT POWER SUPPLY 67

Power supply 67 consists of a battery 70 which includes a plurality of rechargeable cells (such as nickel-cadmium) connected in series between cable connector terminals 101 and 102. Terminals 101 and 102 are coupled to the battery-charging circuit in the support console or to any other suitable battery-charging device. Battery 70 is connected through multiposition slide switches 104 and 105 to the gas-sensing cell of the dosimeter, to the associated electronic circuitry, and to sampling pump 106.

Multiposition "Standby/Operate" slide switch 105, which is ganged with potentiostat switch 66, applies the A+ supply voltage to energize amplifiers 75, 80, 83, 84, 90, 95, and 68 when that switch is in the "operate" position. It also provides the A+ supply voltage for voltage regulator 78. With switch 105 in the "standby" position, the switch armature is in the position shown in FIG. 3 and A+ terminal 107 is disconnected from battery 70. When the switch armature is moved to the upper or "operate" position, the A+ terminal 107 and sampling pump 106 are both connected to battery 70 through armature 104a of ON-OFF switch 104 if switch 104 is in the ON position as shown in FIG. 3. Power to potentiostatic amplifier 60 which applied through A++ terminal 108 is independent of switch 105 so that the sensing cell and potentiostat are energized during "standby".

ON-OFF switch 104, on the other hand, completely disconnects the power supply and de-energizes the dosimeter including potentiostatic amplifier 60 and gas-detecting cell 51 when switch 104 is in the OFF position. Armature 104b of switch 104 is ganged to armature 104a and connects intermediate tap 69 on battery 70 to switch 66 associated with the potentiostat. Thus, movement of switch 104 to the OFF position completely disables the dosimeter circuitry by disconnecting the A++ supply voltage to amplifier 60 of the potentiostat and removing the reference voltage. With switch 104 in the ON position, battery 70 is connected to the dosimeter and switch 105 determines whether the dosimeter is in the "operate" mode with the dosimeter completely energized and oprative, or in the "standby" mode with only the potentiostat and the sensing cell energized.

THE DOSIMETER SUPPORT CONSOLE

Figure 5:
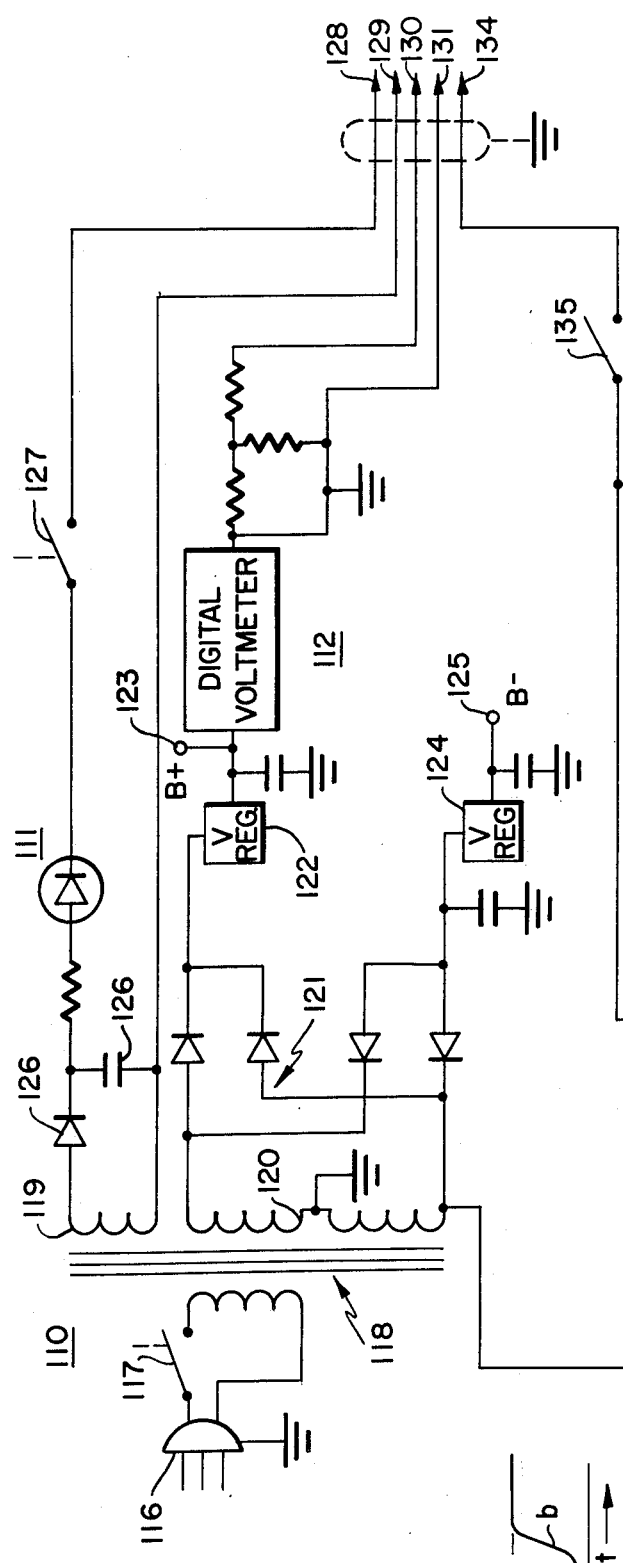
FIG. 5 is a schematic illustration of the electronic circuitry in the support console.

Support console 31 is shown schematically in FIG. 5 and includes, broadly speaking, a power supply 110, a battery charging network 111, a calibrated indicator 112 for showing instantaneous gas concentration, a fixed, reverse calibrated current source 113, and a timing network 114 for providing an indication of the time interval (direct PPM-hour indication) during which the fixed reverse calibrated current flows to reset the coulometer to the zero integral state, so that dosage in PPM-hours may be displayed.

POWER SUPPLY 110 AND BATTERY-CHARGING CIRCUIT 111

Alternating current from a suitable source 116 is coupled through armature 117 of console ON-OFF switch 48 to the primary winding of transformer 118 which has two secondary windings 119 and 120. Secondary winding 120 has a grounded center tap and is coupled to a full-wave rectifying circuit 121 to produce positive and negative unidirectional voltages at the output of rectifying circuit 121. The positive unidirectional voltage is coupled to voltage regulator 122 to provide a regulated positive B+ supply voltage at output terminal 123. The negative unidirectional voltage from rectifying circuit 121 is applied to voltage regulator 124 to produce a regulated negative B— supply voltage at output terminal 125. Secondary winding 119 of transformer 118 is coupled to rectifier 126 which is poled to rectify positive alternations. The half-wave rectified voltage is filtered in capacitor 126 and applied, through armature 127 of console ON-OFF switch 48, to cable connector terminals 128 and 129 which are coupled directly to terminals 101 and 102 of power supply 67 to recharge the nickel-cadmium batteries in battery pack 70 whenever the console cable is connected to the dosimeter.

The regulated positive voltage from regulator 122 is the supply voltage for a digital voltmeter 112. The input to voltmeter 112 is through cable connector terminals 130 and 131 which are connected to dosimeter cable connector terminals 89c and 89b, respectively, shown in FIG. 3. Thus, the output voltage from amplifier 84 in dosage measuring network 73 is applied directly to the digital voltmeter to provide an indication of concentration levels in PPM when the dosimeter is coupled to the console. This is useful in calibrating the dosimeter with a calibrating gas of known concentration, by adjusting the zero and span adjust potentiometers.

CALIBRATED REVERSE CURRENT SOURCE 113

The source of fixed calibrating current for resetting the integrating coulometer and driving it to the zero integral state includes a negative DC regulated voltage source at input terminal 132. This negative voltage is the regulated B— voltage from output terminal 125 of regulator 124. A large resistor 133 is coupled between terminal 132 and cable terminal 134 through switch armature 135 of console reset/read switch 47. Cable terminal 134 is connected directly to the dosimeter cable connector terminal 89a which is connected to integrating coulometer 87. Since the voltage is regulated and is applied to a large resistor of known value, a fixed calibrated current is produced and driven through the coulometer whenever switch armature 135 is closed. This switch is closed when console switch 47 as shown in FIG. 2 is switched to the reset/read position. The reverse calibrating current continues to be driven to the coulometer until the coulometer reaches the zero integral level, at which time all of the silver is deplated and the reverse calibrating current ceases flowing. At this time the voltage across the coulometer rises and this positive going signal is coupled through a cable connected terminal 134 and switch armature 135 to the non-inverting input terminal of amplifier 136.

A clamping diode 137 is connected between the amplifier output and ground to prevent negative going excursions of the amplifier output. The diode is so poled that negative going output voltage excursions drive it into conduction. The amplifier output voltage is thus limied to positive voltages so that the amplifier responds only to the positive going signal from the coulometer when it reached the zero integral level.

The output of amplifier 136 goes positive when the coulometer is reset, and this positive pulse is applied to synchronous counter 114 to terminate counting of the timing or clock pulses from the time interval pulse generator 115. That is, the positive trigger pulse from the coulometer latches counter 114 preventing further counting. The count provides a direct indication of the integrated dosage since each count represents a fixed time period during which the calibrated reverse current has been flowing, so that the total count is the integrated value of the carbon monoxide times the hours, sensed by the dosimeter.

FIXED TIME INTERVAL PULSE GENERATING CIRCUIT 115

The fixed interval pulses are generated in network 115 and then are applied to counter 114. The alternating voltage, from secondary winding 120 of transformer 118 which is typically 60 Hz, is coupled through suitable current limiting resistors to the base of NPN transistor 138. The base of transistor 138 is coupled through diode 139 to ground. Diode 139 is so poled that negative going alternations of the alternating voltage from winding 120 are bipassed to ground. The positive alternations, on the other hand, drive transistor 138 into conduction, producing negative going output pulses at its collector. The period of these pulses is 1/60 sec. for a sixty Hz alternating voltage. These pulses are applied to a frequency divider 140, which includes suitable countdown circuitry. The output of divider 140 is output pulses which have a time duration which is a multiple of that of the input pulses. For example, by using a $2^6$ divider (divide by 64), the period of the output pulses is 1.067 secs. (1/60 × 64).

Counter 114 is enabled and counts pulses from divider 140 only if read/reset switch 47 has been actuated by applying the fixed, reverse, calibrated current to the integrating coulometer in the dosimeter. This, as has been pointed out previously, allows the counter to count the 1.067 second pulses as long as the calibrated current flows. Counting is terminated whenever the integrating coulometer is reset to the zero integral state. Counter 114 may be any one of a number of commercially available counters.

Counter 114 has pulse input and reset terminals P and R and a latching terminal shown generally at 141. Latching terminal 141 is connected through a diode 142 and an impedance network 143 to switch armature 144. Switch armature 144 is ganged to the read-reset switch armature 135 so that switch armature 144 is open when switch armature 135 is closed, and vice versa. When armature 144 is closed, a positive B+ voltage from terminal 145 is applied to reset terminal R, resetting the counter to the zero count. The positive voltage is also applied through diode 142 and to latching terminal 141, and this maintains the counter latched in the zero count. When switch 135 is closed to apply the calibrated reverse current to the coulometer, switch armature 144 is opened, removing the latching voltage which held the counter at the zero count. Counter 114 begins to count the 1.067 sec. pulses from divider 140 which are applied to its pulse input terminal. The counter continues to count as long as calibrated current flows and switch 135 remains closed. When the coulometer reaches the zero integral state, the positive triggering pulse from the coulometer is applied to the non-inverting terminal of amplifier 136. This positive output pulse from amplifier 136 is applied over lead 143 to latching terminal 141 to latch the counter to retain the count at the time the triggering voltage from the coulometer appears. Diode 142 blocks the positive pulse from reset terminal R to prevent the counter from being reset. The count represents the product of time, $t$, and the calibrated current, $i$, and this count (direct reading PPM-hours) is then displayed on a suitable digital display as the integrated value or dosage of carbon monoxide. The dosage is displayed as long as switch armature 135 remains closed, thus keeping switch armature 144 open. Digital display may be cleared by moving console switch 47 to the "zero" position, thereby closing switch armature 144 and opening switch armature 135. This applies a positive voltage to reset terminal R, resetting counter 114, and through diode 142 to latch terminal 141.

It will be apparent from the previous description that a small, sensitive, accurate, and light-weight dosimeter has been provided to provide accurate information as to accumulated exposure to carbon monoxide or any other gas which is to be detected and also provides a visual as well as audible warning whenever the instantaneous gas concentration exceeds predetermined levels for which warnings are desired. Support console flow for providing displays of the integrated dosage is also provided as an adjunct to and part of the overall novel gas dosimeter equipment described herein. While a particular embodiment of this invention has been shown, it will, of course, be understood that the invention is not limited thereto since many modifications, both in the circuit and arrangement and the instrumentalities employed may be made. It is contemplated, by the appended claims, to cover any such modifications forward in a true spirit and scope of this invention.

What I claim is new and desired to secure by Letters Patent of the United States is:

1. A gas dosage instrumentality for measuring the total quantity of a selected gas comprising the combination of;
   (a) a gas-sensing cell for electrochemically converting the selected gas to produce an electrical signal directly related to the concentration of the selected gas,
   (b) means for bringing gaseous samples to said sensing cell,
   (c) means for measuring the total quantity of the selected gas sensed by said cell, including
      (1) a reversible, electrochemical integrating device for continuously storing the signals from said cell to provide a measure of the accumulated quantity of the selected gas, (2) means coupled to said integrating device for selectively applying an electrical resetting signal thereto for readout of the stored information and to reset the integrating device, (3) means responsive to said resetting signal for measuring and indicating the accumulated dosage.

2. The gas dosage instrumentality according to claim 1 wherein said integrating device is an integrating coulometer in which a metal is electrochemically plated onto an electrode in response to the signal from the sensing cell and is electrochemically removed in response to the resetting signal, said coulometer providing a triggering signal when all the metal has been removed and readout is terminated.

3. The gas dosage instrumentality according to claim 2 wherein said reset signal generating means includes a current source for driving a fixed reverse current through said coulometer to remove metal during readout.

4. The gas dosage instrumentality according to claim 3 wherein the dosage measuring and indicating means includes timing means to determine the duration of flow of the fixed, reverse, resetting current, said timing means being actuated upon initiation of reverse current flow and terminated in response to the triggering signal.

5. The gas dosage instrumentality according to claim 1 wherein said gas-sensing cell includes a solid electrolyte, catalytic sensing and counter-electrodes in contact with and positioned on opposite sides of said solid electrolyte, and means for electrically biasing said electrodes to produce electrochemical conversion of the selected gas at said sensing electrode.

6. The gas dosage instrument according to claim 5 wherein said integrating device is an integrating coulometer wherein storage occurs by electrochemical deposition of a material through electron flow into said coulometer, whereby the quantity of deposited material is a direct measure of the amount of gas sensed.

7. The dosage instrument according to claim 6 wherein said reset signal generating means includes a current source for driving a fixed, reverse current through said coulometer to remove deposited metal.

8. The gas dosage instrumentality according to claim 7 including timing means to determine the duration of flow of the fixed, reverse current as a measure of the gas dosage.

9. In a gas dosimeter, the combination comprising,
(a) a gas-sensing cell for electrochemically converting a selected gas to produce an electrical signal directly related to the concentration of that gas,
(b) means for bringing gaseous samples to the cell whereby said cell produces an electrical signal whenever the gaseous samples contain the selected gas,
(c) means to accumulate the total quantity of the selected gas sensed by said cell, including
(1) a reversible electrochemical integrating device capable of storing quantity information by electrochemical deposition of a material in the device by electron flow in one direction through the device, said deposited material being electrochemically removable by electron flow in the opposite direction,
(2) means coupled to said integrating device to convert the signals from said cell to electron flow for electrochemically depositing a material, whereby the quantity of the deposited material is a direct measure of the amount of the selected gas.

10. The gas dosimeter according to claim 9 wherein said cell comprises a non-aqueous, solid electrolyte, a sensing electrode, and a counter-electrode in contact with said solid electrolyte on opposite sides thereof, and means coupling said cell to said integrating device.

11. The gas dosimeter according to claim 10 including means to produce an indication when the output signal from said cell shows that the concentration of the selected gas sensed by the cell exceeds a predetermined level.

12. The gas dosimeter according to claim 10 wherein the integrating coulometer in which a metal is electrochemically plated onto an electrode in response to electron flow in said one direction and removed from the electrode in response to electron flow in the other direction.

13. The gas dosimeter according to claim 10 wherein the non-aqueous electrolyte in said gas-sensing cell is an ion exchange membrane and the said sensing and counterelectrodes are positioned on opposite sides of said membrane.

14. The gas dosimeter according to claim 13 wherein said cell includes a reference electrode on the same side of the said membrane as the sensing electrode, potentiostatic circuit means interconnecting said sensing, reference and counterelectrodes to maintain the potentials at the potential differences between said electrodes such as to produce rapid electrochemical conversion of the selected gas without interference due to electrochemical conversion of other gases or due to water.

15. The gas dosimeter according to claim 14 including further means for selectively maintaining said cell partially energized in a non-sensing mode of operation and fully energized in a sensing mode whereby said dosimeter rapidly reaches the sensing mode and has low power dissipation in the non-sensing mode.

* * * * *